United States Patent
Nishino et al.

(10) Patent No.: US 7,619,084 B2
(45) Date of Patent: Nov. 17, 2009

(54) PROCESS FOR PREPARING 4-AMINOPYRIMIDINE COMPOUND

(75) Inventors: Shigeyoshi Nishino, Ube (JP); Kenji Hirotsu, Ube (JP); Hidetaka Shima, Ube (JP); Takashi Harada, Ube (JP)

(73) Assignee: UBE Industries, Ltd., Ube-shi (JP)

( * ) Notice: Subject to any disclaimer, the term of this patent is extended or adjusted under 35 U.S.C. 154(b) by 125 days.

(21) Appl. No.: 11/666,510

(22) PCT Filed: Oct. 28, 2005

(86) PCT No.: PCT/JP2005/019878

§ 371 (c)(1),
(2), (4) Date: Apr. 27, 2007

(87) PCT Pub. No.: WO2006/046691

PCT Pub. Date: May 4, 2006

(65) Prior Publication Data

US 2008/0045712 A1 Feb. 21, 2008

(30) Foreign Application Priority Data

Oct. 28, 2004 (JP) ............... 2004-313290
Oct. 28, 2004 (JP) ............... 2004-313291
Jun. 2, 2005 (JP) ............... 2005-162335

(51) Int. Cl.
*C07D 239/02* (2006.01)
(52) U.S. Cl. .................................... 544/326
(58) Field of Classification Search ................. 544/326
See application file for complete search history.

(56) References Cited

U.S. PATENT DOCUMENTS 4,539,403 A 9/1985 Fujii et al.

FOREIGN PATENT DOCUMENTS

| JP | 46-22157 A | 6/1971 |
| JP | 58-134081 A | 8/1983 |
| JP | 58-172375 A | 10/1983 |
| JP | 60-109572 A | 6/1985 |
| JP | 2003-64056 A | 3/2003 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*

* cited by examiner

*Primary Examiner*—James O Wilson
*Assistant Examiner*—Douglas M Willis
(74) *Attorney, Agent, or Firm*—Birch, Stewart, Kolasch & Birch, LLP

(57) ABSTRACT

The present invention is to provide a process for preparing a 4-aminopyrimidine compound represented by the formula (3):

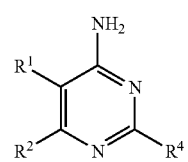

(3)

wherein $R^1$ and $R^2$ each represent a hydrogen atom or group which does not participate in the reaction and which may have a substituent(s), and $R^1$ and $R^2$ may be bonded to each other to form a ring, and $R^4$ represents a hydrogen atom or a hydrocarbon group,
which comprises reacting ammonia, a 3-substituted or unsubstituted acrylonitrile compound represented by the formula (1):

$$CR^1(CN){=}CR^2Y \qquad (1)$$

wherein $R^1$ and $R^2$ have the same meanings as defined above, and Y represents an amino group or OR, where R represents a hydrogen atom or a hydrocarbon group,
and an organic acid compound represented by the formula (2):

$$(R^3O)_3CR^4 \qquad (2)$$

wherein $R^3$ represents a hydrocarbon group, and $R^4$ has the same meaning as defined above.

13 Claims, No Drawings

PROCESS FOR PREPARING 4-AMINOPYRIMIDINE COMPOUND

BACKGROUND OF THE INVENTION

1. Field of the Invention

The present invention relates to a process for preparing a 4-aminopyrimidine compound from a 3-substituted or unsubstituted acrylonitrile compound. The 4-aminopyrimidine compound is a compound useful as a starting material or a synthetic intermediate for a medicine, an agricultural chemical, etc.

2. Description of Related Art

Heretofore, as a method for preparing a 4-aminopyrimidine compound, there is described a method, for example, of reacting formamide and an amide compound in the presence of phosphorus oxychloride to prepare various 4-aminopyrimidine compounds with yields of 6 to 32% (for example, see Patent Literature 1). However, in this method, there are problems that formamide having terato-genicity or phosphorus oxychloride having high toxicity must be used, and yet, yield is extremely low, so that this is not advantageous as an industrial method for preparing a 4-aminopyrimidine compound.

Patent literature 1: Japanese Patent Publication No. Sho.46-22157

An object of the present invention is, namely, to solve the above-mentioned problems, and to provide an industrially suitable process for preparing a 4-aminopyrimidine compound which can prepare the 4-aminopyrimidine compound under mild conditions with simple and easy method.

BRIEF SUMMARY OF THE INVENTION

The present invention relates to a process for preparing a 4-aminopyrimidine compound represented by the formula (3):

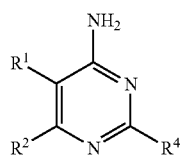

wherein $R^1$ and $R^2$ each represent a hydrogen atom or group which does not participate in the reaction and which may have a substituent(s), and $R^1$ and $R^2$ may be bonded to each other to form a ring, and $R^4$ represents a hydrogen atom or a hydrocarbon group, which comprises reacting ammonia, a 3-substituted or unsubstituted acrylonitrile compound represented by the formula (1):

$$CR^1(CN)=CR^2Y \quad (1)$$

wherein $R^1$ and $R^2$ have the same meanings as defined above, and Y represents an amino group or OR, where R represents a hydrogen atom or a hydrocarbon group, and an organic acid compound represented by the formula (2):

$$(R^3O)_3CR^4 \quad (2)$$

wherein $R^3$ represents a hydrocarbon group, and $R^4$ has the same meaning as defined above.

According to the present invention, an industrially suitable process for preparing a 4-aminopyrimidine compound can be provided, which can prepare a 4-aminopyrimidine compound under mild conditions and a simple and easy method.

DETAILED DESCRIPTION OF THE INVENTION

In the 3-substituted or unsubstituted acrylonitrile compound to be used in the reaction of the present invention, there exist stereoisomers represented by the following formula (1a) or (1b), and either of the isomers and a mixture thereof with an optional ratio can be preferably used in the present invention.

wherein $R^1, R^2$ and Y have the same meanings as defined above

In the formula (1), when it is a 3-oxyacrylonitrile compound where Y is represented by OR, the R is a hydrogen atom or a hydrocarbon group. As the hydrocarbon group, there may be more specifically mentioned, for example, an alkyl group such as a methyl group, ethyl group, propyl group, butyl group, pentyl group, hexyl group, heptyl group, octyl group, nonyl group, decyl group, etc.; a cycloalkyl group such as a cyclopropyl group, cyclobutyl group, cyclopentyl group, cyclohexyl group, cycloheptyl group, cyclooctyl group, etc.; an aralkyl group such as a benzyl group, phenethyl group, phenylpropyl group, etc.; an aryl group such as a phenyl group, p-tolyl group, naphthyl group, anthryl group, etc. Incidentally, these groups contain various kinds of isomers.

In the 3-substituted or unsubstituted acrylonitrile compound to be used in the reaction of the present invention, when Y is an amino group, it is a 3-amino-acrylonitrile compound. In the formula (1), $R^1$ and $R^2$ are each a hydrogen atom or a group which does not participate in the reaction and which may have a substituent(s), and more specifically, there may be mentioned, for example, an alkyl group, cycloalkyl group, aralkyl group, aryl group, halogen atom, hydroxyl group, alkoxyl group, alkylthio group, nitro group, cyano group, carbonyl group, amino group or carboxyl group. Incidentally, $R^1$ and $R^2$ may be bonded to each other to form a ring.

As the above-mentioned alkyl group, there may be mentioned, for example, a methyl group, ethyl group, propyl group, butyl group, pentyl group, hexyl group, heptyl group, octyl group, nonyl group, decyl group, etc. Incidentally, these groups contain various kinds of isomers.

As the above-mentioned cycloalkyl group, there may be mentioned, for example, a cyclopropyl group, cyclobutyl group, cyclopentyl group, cyclohexyl group, cycloheptyl group, cyclooctyl group, etc.

As the above-mentioned aralkyl group, there may be mentioned, for example, a benzyl group, phenethyl group, phenylpropyl group, etc. Incidentally, these groups contain various kinds of isomers.

As the above-mentioned aryl group, there may be mentioned, for example, a phenyl group, p-tolyl group, naphthyl group, anthryl group, etc. Incidentally, these groups contain various kinds of isomers.

As the above-mentioned halogen atom, there may be mentioned, for example, a fluorine atom, chlorine atom, bromine atom and iodine atom.

As the above-mentioned alkoxyl group, there may be mentioned, for example, a methoxyl group, ethoxyl group, propoxyl group, etc. Incidentally, these groups contain various kinds of isomers.

As the above-mentioned alkylthio group, there may be mentioned, for example, a methylthio group, ethylthio group, propylthio group, etc. Incidentally, these groups contain various kinds of isomers.

The above-mentioned alkyl group, cycloalkyl group, aralkyl group, aryl group, alkoxyl group and alkylthio group may have a substituent(s). As the substituent(s), there may be mentioned a substituent(s) formed through a carbon atom, a substituent(s) formed through an oxygen atom, a substituent (s) formed through a nitrogen atom, a substituent(s) formed through a sulfur atom, a halogen atom, etc.

As the above-mentioned substituent(s) formed through a carbon atom, there may be mentioned, for example, an alkyl group such as a methyl group, ethyl group, propyl group, butyl group, pentyl group, hexyl group, etc.; a cycloalkyl group such as a cyclopropyl group, cyclobutyl group, cyclopentyl group, cyclohexyl group, cyclobutyl group, etc.; an alkenyl group such as a vinyl group, allyl group, propenyl group, cyclopropenyl group, cyclobutenyl group, cyclopentenyl group, etc.; a heterocyclic group such as a quinolyl group, pyridyl group, pyrrolidyl group, pyrrolyl group, furyl group, thienyl group, etc.; an aryl group such as a phenyl group, tolyl group, fluorophenyl group, xylyl group, biphenyl group, naphthyl group, anthryl group, phenanthryl group, etc.; an acyl group (which may be in a form of acetal) such as an acetyl group, propionyl group, acryloyl group, pivaloyl group, cyclohexylcarbonyl group, benzoyl group, naphthoyl group, toluoyl group, etc.; a carboxyl group; an alkoxycarbonyl group such as a methoxycarbonyl group, ethoxycarbonyl group, etc.; an aryloxycarbonyl group such as a phenoxycarbonyl group, etc.; a halogenated alkyl group such as a trifluoromethyl group, etc.; and a cyano group. Incidentally, these groups contain various kinds of isomers.

As the above-mentioned substituent(s) formed through an oxygen atom, there may be mentioned, for example, a hydroxyl group; an alkoxyl group such as a methoxyl group, ethoxyl group, propoxyl group, butoxyl group, pentyloxyl group, hexyloxyl group, heptyloxyl group, benzyloxyl group, etc.; an aryloxyl group such as a phenoxyl group, toluoyloxyl group, naphthyloxyl group, etc. Incidentally, these groups contain various kinds of isomers.

As the above-mentioned substituent(s) formed through a nitrogen atom, there may be mentioned, for example, a primary amino group such as a methylamino group, ethylamino group, butylamino group, cyclohexylamino group, phenylamino group, naphthylamino group, etc.; a secondary amino group such as a dimethylamino group, diethylamino group, dibutylamino group, methylethylamino group, methylbutylamino group, diphenylamino group, N-methyl-N-methanesulfonylamino group, etc.; a heterocyclic amino group such as a morpholino group, piperidino group, piperadinyl group, pyrazolidinyl group, pyrrolidino group, indolyl group, etc.; and an imino group. Incidentally, these groups contain various kinds of isomers.

As the above-mentioned substituent(s) formed through a sulfur atom, there may be mentioned, for example, a mercapto group; a thioalkoxyl group such as a thiomethoxyl group, thioethoxyl group, thiopropoxyl group, etc.; a thioaryloxyl group such as a thiophenoxyl group, thiotoluoyloxyl group, thionaphthyloxyl group, etc., and the like. Incidentally, these groups contain various kinds of isomers.

As the above-mentioned halogen atom, there may be mentioned a fluorine atom, chlorine atom, bromine atom and iodine atom.

The organic acid compound to be used in the reaction of the present invention is represented by the above-mentioned formula (2). In the formula (2), $R^3$ is a hydrocarbon group, more specifically, there may be mentioned, for example, an alkyl group such as a methyl group, ethyl group, propyl group, butyl group, pentyl group, hexyl group, heptyl group, octyl group, nonyl group, decyl group, etc.; a cycloalkyl group such as a cyclopropyl group, cyclobutyl group, cyclopentyl group, cyclohexyl group, cycloheptyl group, cyclooctyl group, etc.; an aralkyl group such as a benzyl group, phenethyl group, phenylpropyl group, etc.; and an aryl group such as a phenyl group, p-tolyl group, naphthyl group, anthryl group, etc., preferably an alkyl group, more preferably a methyl group and an ethyl group. Incidentally, these groups contain various kinds of isomers.

Also, $R^4$ is a hydrogen atom or the same meaning as the hydrocarbon group represented by the above-mentioned $R^3$. Such organic acid compounds may be mentioned, for example, methyl orthoformate, ethyl orthoformate, methyl orthoacetate, ethyl orthoacetate, methyl orthopropionate, ethyl orthopropionate, methyl orthobutyrate, ethyl orthobutyrate, methyl orthobenzoate and ethyl orthobenzoate, etc., and at least one selected from the group consisting of these compounds is optionally used.

An amount of the above-mentioned organic acid compound to be used is preferably 1.0 to 15 mols, more preferably 1.1 to 5.0 mols based on 1 mol of the 3-substituted or unsubstituted acrylonitrile compound.

The reaction of the present invention is carried out in the presence or in the absence of a solvent. As the solvent to be used, it is not particularly limited so long as it does not inhibit the reaction, and there may be mentioned, for example, an alcohol such as methanol, ethanol, isopropyl alcohol, n-butyl alcohol, t-butyl alcohol, n-pentyl alcohol, etc.; an amide such as N,N-dimethylformamide, N-methylpyrrolidone, etc.; a urea such as N,N'-dimethylimidazolidinone, etc.; a sulfoxide such as dimethylsulfoxide, etc.; an aromatic hydrocarbon such as benzene, toluene, xylene, mesitylene, etc.; an ether such as diethyl ether, tetrahydrofuran, dioxane, etc., preferably an alcohol and an amide, and more preferably methanol, ethanol and N,N'-dimethylimidazolidinone are used. Incidentally, these solvents may be used singly or in combination of two or more kinds.

An amount of the above-mentioned solvent to be used may be optionally adjusted depending on a degree of uniformity or condition of stirring of the reaction mixture, and it is preferably 0 to 50 g, more preferably 0 to 20 g, particularly preferably 0 to 5 g based on 1 g of the 3-substituted or unsubstituted acrylonitrile compound.

An amount of the ammonia to be used in the reaction of the present invention is preferably 1.0 to 100 mols, more preferably 1.1 to 40 mols, particularly preferably 2.0 to 40 mols, most preferably 2.1 to 40 mols based on 1 mol of the 3-substituted or unsubstituted acrylonitrile compound. Incidentally, a state of the ammonia to be used is not particularly limited, and may be either state of a gas or a liquid, and it may be used as a solution of an organic solvent (for example, an alcohol). Incidentally, the ammonia and an ammonia solution in these states may be used alone or in admixture of two or more.

The reaction of the present invention can be carried out by the method, for example, in which the 3-substituted or unsubstituted acrylonitrile compound, the organic carboxylic acid compound and a solvent are mixed in the presence of ammonia and stirred, etc. A reaction temperature at that time is preferably 40 to 250° C., more preferably 50 to 200° C., and a reaction pressure is not particularly limited.

Incidentally, the 4-aminopyrimidine compound obtained by the reaction of the present invention can be isolated and purified by a general method, for example, neutralization, extraction, filtration, concentration, distillation, recrystallization, crystallization column chromatography, etc., after completion of the reaction.

EXAMPLES

Next, the present invention will be explained more specifically by referring to Examples, but the scope of the present invention is not limited by these.

Example 1

Synthesis of 4-aminopyrimidine

In a pressure-resistant vessel made of stainless steel, equipped with a stirring device, a reflux condenser and a thermometer and having an inner volume of 1000 ml were charged 83.0 g (1.0 mol) of 3-methoxyacrylonitrile, 212 g (2.0 mols) of methyl orthoformate and 355 g (2.5 mols) of 12% by weight ammonia-isopropyl alcohol solution, and the mixture was reacted under stirring at 145° C. for 12 hours. After completion of the reaction, when a part (about 5 ml) of the obtained reaction mixture was analyzed by gas chromatography (absolute quantitative method), it was found that 67.3 g (Reaction yield: 70.8%) of 4-aminopyrimidine was formed. Then, the reaction mixture was concentrated under reduced pressure, 54.8 g of activated carbon and 747 ml of isopropyl alcohol were added to the concentrate, and the mixture was stirred at 90° C. for 1 hour. After completion of the stirring, the mixture was filtered, and the filtrate was concentrated under reduced pressure. This operation of treating with activated carbon was repeated twice. After completion of the stirring, the mixture was filtered, and the filtrate was concentrated under reduced pressure. To the concentrate were added 125 ml of isopropyl alcohol and 665 ml of toluene, the temperature of the mixture was raised to 90° C. to make a uniform solution, and then, cooled to 0° C. to precipitate crystals. The obtained crystals were filtered and dried to obtain 44.2 g (Isolation yield: 46.5%) of 4-aminopyrimidine with purity of 99.9% (Areal percentage by gas chromatography) as white crystals.

Physical properties of the 4-aminopyrimidine were as follows.

$^1$H-NMR (CDCl$_3$, δ (ppm)); 6.46 (1H, d, J=6.0 Hz), 6.81 (2H, brs), 8.03 (1H, d, J=6.0 Hz), 8.33 (1H, d, J=0.7 Hz) CI-MS (m/e); 96 (M+1)

Example 2

Synthesis of 4-aminopyrimidine

In a pressure-resistant vessel made of stainless steel, equipped with a stirring device, a reflux condenser and a thermometer and having an inner volume of 1000 ml were charged 90.0 g (1.1 mols) of 3-methoxyacrylonitrile, 230 g (2.2 mols) of methyl orthoformate and 351 g (4.3 mols) of 21% by weight ammonia-methanol solution, and the mixture was reacted under stirring at 145° C. for 6.5 hours. After completion of the reaction, when the reaction mixture was analyzed by gas chromatography, it was found that 72.7 g (Reaction yield: 70.6%) of 4-aminopyrimidine was formed.

Example 3

Synthesis of 4-aminopyrimidine

In a pressure-resistant vessel made of stainless steel, equipped with a stirring device, a reflux condenser and a thermometer and having an inner volume of 300 ml were charged 14.4 g (173 mmol) of 3-methoxyacrylonitrile, 38.5 g (260 mmol) of ethyl orthoformate and 74.9 g (519 mmol) of 11.8% by weight ammonia-isopropyl alcohol solution, and the mixture was reacted under stirring at 150° C. for 9 hours. After completion of the reaction, when the reaction mixture was analyzed by gas chromatography, it was found that 12.0 g (Reaction yield: 72.7%) of 4-aminopyrimidine was formed.

Example 4

Synthesis of 2-methyl-4-aminopyrimidine

In a pressure-resistant vessel made of stainless steel having an inner volume of 10 ml were charged 1.0 g (12 mmol) of 3-methoxyacrylonitrile, 3.9 g (32 mmol) of methyl orthoacetate and 4.0 g (56 mmol) of 24% by weight ammonia-methanol solution, and the mixture was reacted under stirring at 130° C. for 8 hours. After completion of the reaction, 20 ml of hexane was added to the reaction mixture, and the mixture was stirred and then filtered to obtain 0.94 g (Isolation yield: 72%) of 2-methyl-4-aminopyrimidine as yellow crystals.

Physical properties of the 2-methyl-4-aminopyrimidine were as follows.

$^1$H-NMR (DMSO-d$_6$, δ (ppm)); 2.29 (3H, s), 6.22 (1H, dd, J=5.9, 0.5 Hz), 6.69 (2H, brs), 7.94 (1H, d, J=5.9 Hz) CI-MS (m/e); 109 (M+1)

Example 5

Synthesis of 6-methyl-4-aminopyrimidine

In a pressure-resistant vessel made of stainless steel having an inner volume of 10 ml were charged 1.0 g (11.7 mmol) of 3-aminocrotonnitrile with purity of 96%, 2.48 g (23.4 mmol) of methyl orthoformate and 1.42 g (17.5 mmol) of 21% by weight ammonia-methanol solution, and the mixture was reacted under stirring at 130° C. for 15 hours. After completion of the reaction, the reaction mixture was concentrated under reduced pressure, 10 ml of isopropyl alcohol and 660 mg of activated carbon were added to the concentrate, and the mixture was stirred at 90° C. for 1 hour and then filtered. To the resulting filtrate was added 660 mg of activated carbon, and the mixture was again stirred at 90° C. for 1 hour. After filtration, the filtrate was concentrated, 1.8 ml of isopropyl alcohol and 3 ml of toluene were added to the concentrate, and the resulting mixture was heated up to 90° C., and gradually cooled and stirred at −5° C. for 1 hour. The precipitated solid was collected by filtration, and the solid was dried under reduced pressure to obtain 326 mg (Isolation yield; 26%) of 6-methyl-4-aminopyrimidine with purity of 99.5% (Areal percentage by gas chromatography) as white crystals.

Physical properties of the 6-methyl-4-aminopyrimidine were as follows.

$^1$H-NMR (DMSO-$d_6$, δ (ppm)); 2.17 (3H, s), 6.25 (1H, s), 6.65 (2H, brs), 8.21 (1H, s) CI-MS (m/e); 110 (M+1)

The present invention relates to a process for preparing a 4-aminopyrimidine compound from a 3-substituted or unsubstituted acrylonitrile compound. The 4-aminopyrimidine compound is a useful compound as a starting material or a synthetic intermediate for a medicine, agricultural chemical, etc., and can be used for preparing an amide derivative useful as a medicine according to the method as described in, for example, Japanese Unexamined Patent Publication No. 2003-64056.

The invention claimed is:

1. A process for preparing a 4-aminopyrimidine compound represented by the formula (3):

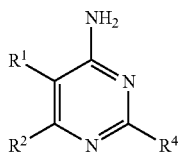
(3)

wherein $R^1$ and $R^2$ each represent a hydrogen atom, methyl group, ethyl group, propyl group, butyl group, pentyl group, hexyl group, heptyl group, octyl group, nonyl group or decyl group where the propyl group, butyl group, pentyl group, hexyl group, heptyl group, octyl group, nonyl group and decyl group each contain isomers thereof, and $R^4$ represents a hydrogen atom, methyl group, ethyl group, propyl group, butyl group, pentyl group, hexyl group, heptyl group, octyl group, nonyl group or decyl group where the propyl group, butyl group, pentyl group, hexyl group, heptyl group, octyl group, nonyl group and decyl group each contain isomers thereof, which comprises reacting ammonia, a 3-substituted acrylonitrile compound represented by the formula (1):

wherein $R^1$ and $R^2$ have the same meanings as defined above, and Y represents an amino group or OR, where R represents a hydrogen atom, methyl group, ethyl group, propyl group, butyl group, pentyl group, hexyl group, heptyl group, octyl group, nonyl group or decyl group where the propyl group, butyl group, pentyl group, hexyl group, heptyl group, octyl group, nonyl group and decyl group each contain isomers thereof, and an organic acid compound represented by the formula (2):

wherein $R^3$ represents a methyl group, ethyl group, propyl group, butyl group, pentyl group, hexyl group, heptyl group, octyl group, nonyl group or decyl group where the propyl group, butyl group, pentyl group, hexyl group, heptyl group, octyl group, nonyl group and decyl group each contain isomers thereof, and $R^4$ has the same meaning as defined above.

2. The preparation process according to claim 1, wherein ammonia is used in an amount of 1.0 to 100 mols based on 1 mol of the 3-substituted acrylonitrile compound.

3. The preparation process according to claim 1, wherein ammonia is used in an amount of 1.1 to 40 mols based on 1 mol of the 3-substituted acrylonitrile compound.

4. The preparation process according to claim 1, wherein the organic acid compound is used in an amount of 1.0 to 15 mols based on 1 mol of the 3-substituted acrylonitrile compound.

5. The preparation process according to claim 1, wherein the organic acid compound is used in an amount of 1.1 to 5.0 mols based on 1 mol of the 3-substituted acrylonitrile compound.

6. The preparation process according to claim 1, wherein the reaction is carried out at 40 to 250° C.

7. The preparation process according to claim 1, wherein the reaction is carried out at 50 to 200° C.

8. The preparation process according to claim 1, wherein the 3-substituted substituted acrylonitrile compound is a 3-oxyacrylonitrile compound or 3-aminoacrylonitrile compound.

9. The preparation process according to claim 8, wherein the 3-oxyacrylonitrile compound is at least one selected from the group consisting of 3-methoxyacrylonitrile, 3-ethoxyacrylonitrile, 3-propoxyacrylonitrile and 3-butoxyacrylonitrile.

10. The preparation process according to claim 1, wherein the organic acid compound is at least one selected from the group consisting of methyl orthoformate, ethyl orthoformate, methyl orthoacetate, ethyl orthoacetate, methyl orthopropionate, ethyl orthopropionate, methyl orthobutyrate and ethyl orthobutyrate.

11. The preparation process according to claim 1, wherein the organic acid compound is methyl orthoformate or ethyl orthoformate.

12. The preparation process according to claim 1, wherein $R^1$ and $R^2$ each represent a hydrogen atom, methyl group, ethyl group, propyl group or butyl group where the propyl group and butyl group each contain isomers thereof, Y represents an amino group or OR, where R represents a hydrogen atom, methyl group, ethyl group, propyl group or butyl group where the propyl group and butyl group each contain isomers thereof, $R^3$ represents a methyl group, ethyl group, propyl group or butyl group where the propyl group and butyl group each contain isomers thereof, and $R^4$ represents a hydrogen atom, methyl group, ethyl group, propyl group or butyl group where the propyl group and butyl group each contain isomers thereof.

13. The preparation process according to claim 1, wherein $R^1$ and $R^2$ each represent a hydrogen atom, methyl group or ethyl group, Y represents an amino group or OR, where R represents a hydrogen atom, methyl group or ethyl group, $R^3$ represents a methyl group or ethyl group, and $R^4$ represents a hydrogen atom, methyl group or ethyl group.

* * * * *